(12) United States Patent
Mori et al.

(10) Patent No.: US 9,127,290 B2
(45) Date of Patent: Sep. 8, 2015

(54) RICE GENE CAPABLE OF IMPARTING WIDE-SPECTRUM DISEASE RESISTANCE

(75) Inventors: Masaki Mori, Ibaraki (JP); Nagao Hayashi, Ibaraki (JP); Shoji Sugano, Ibaraki (JP); Hiroshi Takatsuji, Ibaraki (JP); Hirohiko Hirochika, Ibaraki (JP); Kenji Oda, Okayama (JP); Minami Matsui, Kanagawa (JP)

(73) Assignees: National Institute of Agrobiological Sciences, Ibaraki (JP); Riken, Saitama (JP)

( * ) Notice: Subject to any disclaimer, the term of this patent is extended or adjusted under 35 U.S.C. 154(b) by 218 days.

(21) Appl. No.: 13/061,396

(22) PCT Filed: Mar. 4, 2009

(86) PCT No.: PCT/JP2009/054081
§ 371 (c)(1),
(2), (4) Date: Jun. 24, 2011

(87) PCT Pub. No.: WO2010/023974
PCT Pub. Date: Mar. 4, 2010

(65) Prior Publication Data
US 2011/0258737 A1    Oct. 20, 2011

(30) Foreign Application Priority Data

Aug. 27, 2008  (JP) ................................ 2008-217603

(51) Int. Cl.
| | |
|---|---|
| *A01H 5/00* | (2006.01) |
| *C12Q 1/02* | (2006.01) |
| *C12N 15/82* | (2006.01) |
| *C12N 5/10* | (2006.01) |
| *C12N 9/12* | (2006.01) |
| *G01N 33/50* | (2006.01) |

(52) U.S. Cl.
CPC .............. *C12N 15/8281* (2013.01); *C12N 9/12* (2013.01); *C12N 15/8282* (2013.01); *G01N 33/5097* (2013.01); *G01N 2333/195* (2013.01); *G01N 2500/10* (2013.01)

(58) Field of Classification Search
CPC .. C12N 15/8281; C12N 15/8282; C12N 9/12; G01N 33/5097; G01N 2333/195; G01N 2500/10
USPC ......................................................... 800/279
See application file for complete search history.

(56) References Cited

U.S. PATENT DOCUMENTS

2004/0123343 A1* 6/2004 La Rosa et al. ............... 800/278
2006/0123505 A1  6/2006 Kikuchi et al.

FOREIGN PATENT DOCUMENTS

WO    WO 03/000898 A1    1/2003
WO    WO 2008/070179 A2    6/2008

OTHER PUBLICATIONS

Pedley et al. 2003. Molecular basis of Pto-mediated resistance to bacterial speck disease in tomato. Annu. Rev. Phytopathol. 41:215-243.*
Rowland et al. 2005. Functional analysis of Avr9/Cf-9 rapidly elicited genes identifies a protein kinase, ACIK1, that is essential for full Cf-9-dependent disease resistance in tomato. Plant Cell. 17:295-310.*
GenBank. Accession BAG91730. Accessed Jan. 25, 2013. First uploaded 2001.*
Broglie et al. Transgenic plants with enchanced resistance to the fungal pathogen *Rhizoctonia solani*. 1991. Science. 254:1194-1197.*
Bent. *Arabidopsis* in planta transformation. Uses, mechanisms, and prospects for transformation of other species. 2000. Plant Phys. 124:1540-1547.*
Zhang et al. Transgenic elite Indica rice varieties, resistant to *Xanthomonas oryzae* pv. oryzae. 1998. Mol. Breed. 4:551-558.*
Kachroo et al. Induction of H2O2 in transgenic rice leads to cell death and enhanced resistance to both bacterial and fungal pathogens. 2003. Transgen. Res. 12:577-586.*
Becker, D., "Binary Vectors Which Allow the Exchange of Plant Selectable Markers and Report Genes," Nucleic Acids Research, 1990, p. 203, vol. 18, No. 1.
Cao, H. et al., "The *Arabidopsis NPR*1 Gene That Controls Systemic Acquired Resistance Encodes a Novel Protein Containing Ankyrin Repeats," Cell, Jan. 10, 1997, pp. 57-63, vol. 88.
Dubouzet, J.G. et al, "Ine-Nazuna FOX Keito 2 Man Keito yori Senbatsu sareta Byogen Saikin Pst3000 Kansen Teikosei Idenshi no Kaiseki," Dai 49 Kai Proceedings of the Annual Meeting of the Jap, Mar. 15, 2008, p. 336, Abstract P397(932). ). (Please see International Search Report as a concise Explanation of the Relevance).
Dubouzet, J.G. et al, "Functional Analyses of Rice Genes in 20,000 Rice—*Arabidopsis* FOX Lines Showing Resistance to Bacterial Pathogen *Pst* 3000," Presentation in the 49th Annual Meeting of the Japanese Society of Plant Physiologists, Mar. 20, 2008, 1 page. (with English abstract).
Ichikawa, T. et al., "The FOX Hunting System: An Alternative Gain-of-Function Gene Hunting Technique," The Plant Journal, 2006, pp. 974-985, vol. 45.

(Continued)

*Primary Examiner* — Li Zheng
(74) *Attorney, Agent, or Firm* — Fenwick & West LLP

(57) ABSTRACT

A three-step screening of selection for resistance against pathogenic bacteria infection, selection for resistance against pathogenic fungi infection, and selection for sensitivity to salicylic acid was carried out on *Arabidopsis thaliana* lines highly expressing rice full-length cDNA (rice-FOX *Arabidopsis* lines) which were prepared by using a FOX hunting system. As a result, one *Arabidopsis thaliana* line (line K15424) selected in all of the three types of screening was successfully selected. Line K15424 carries a rice full-length cDNA. Rice overexpressing AK070024 was produced, and resistance against rice bacterial leaf blight was assayed using the T1 generation. As a result, it was confirmed that AK070024-overexpressing rice is resistant against bacterial leaf blight and blast.

8 Claims, 5 Drawing Sheets

(56) References Cited

OTHER PUBLICATIONS

Kanno, M. et al., "Ine-Shiroinunazuna FOX Keito o Mochiita Ine no Yudo Teikosei no Kan'yo suru Shinki Inshi no Tansaku," Dai 49 Kai Proceedings of the Annual Meeting of the Japanese Society of Plant Physiologists, Mar. 15, 2008, p. 335, Abstract P396(931).(Please see International Search Report as a concise Explanation of the Relevance).

Kikuchi, S. et al., "Collection, Mapping, and Annotation of Over 28,000 cDNA Clones from *japonica* Rice," The Rice Full-Length cDNA Consortium, Science, Jul. 18, 2003, pp. 376-379, vol. 301.

Maeda, S. et al., "Ine Kanzencho cDNA Ko Hatsugen Shiroinunazuna Keito o Mochiita Byogen Shijokin C. higginsianum Kansen Teikosei Keito no Senbatsu to Kaiseki," Japan Society for Bioscience, Biotechnology, and Agrochemistry 2008 Nendo (Heisei 20 Nendo) Taikai Koen Yoshishu, Mar. 5, 2008, p. 65, Abstract 2A16a14. ). (Please see International Search Report as a concise Explanation of the Relevance).

Maeda, S. et al., "Screening for Resistance to Fungal Pathogen *Colletotrichum higginsianum* in Transgenic *Arabidopsis* Overexpressing Rice Full-Length cDNA and Molecular Characterization of the Resistant Lines," Presentation in the Japan Society for Bioscience, Biotechnology, and Agrochemistry 2008, Mar. 27, 2008, 20 pages.

Matsui, M. et al, "Ine-Nazuna Fox hunting-kei: Yuyo Keishitsu no Kosoku Tansaku no Tameno Model System," Dai 49 Kai Proceedings of the Annual Meeting of the Japanese Society of Plant Physiologists, Mar. 15, 2008, p. 89, Abstract S09-1(S51). ). (Please see International Search Report as a concise Explanation of the Relevance).

Matsui, M. et al., "Rice FOX Hunting, a Model for Rapid and Systematical Identification of Useful Traits Using Rice Full-Length cDNA Over-Expressors," Presentation in the 49$^{th}$ Annual Meeting of the Japanese Society of Plant Physiologists, Mar. 22, 2008, 30 pages.

Mori, M. et al., "Isolation and Molecular Characterization of a *Spotted Leaf* 18 Mutant by Modified Activation-Tagging in Rice," Plant Mol. Biol., 2007, pp. 847-860, vol. 63.

Nakamura, H. et al., "A Genome-Wide Gain-of-Function Analysis of Rice Genes Using the FOX-Hunting System," Plant Mol. Biol., 2007, pp. 357-371, vol. 65.

Ohyanagi, H. et al., "*Oryza sativa* (japonica cultivar-group) Os09g0533600 (Os09g0533600) mRNA, complete cds.," GenBank Accession NM_001070305 [online], GI: 115480352, Feb. 14, 2008, updated, Retrieved from the Internet [Retrieved on Apr. 28, 2009], http://www.ncbi.nlm.nih.gov/nuccore/115480352?report=genbank. (Please see International Search Report as a concise Explanation of the Relevance).

PCT International Search Report, PCT Application No. PCT/JP2009/054081, May 19, 2009, 2 pages.

PCT International Preliminary Examination Report, PCT Application No. PCT/JP2009/054081, Apr. 21, 2011, 8 pages.

Sugano, S. et al., "Screening for Novel Components Involved in Induced Disease Resistance of Rice Using Rice—*Arabidopsis* FOX Lines," Presentation in the 49$^{th}$ Annual Meeting of the Japanese Society of Plant Physiologists, Mar. 20, 2008, 1 page. (with English abstract).

Taji, T. et al., "Important Roles of Drought- and Cold-Inducible Genes for Galactinol Synthase in Stress Tolerance in *Arabidopsis thaliana*," The Plant Journal, 2002, pp. 417-426, vol. 29, No. 4.

Toki, S. et al., "Early Infection of *Scutellum* Tissue with *Agrobacterium* Allows High-Speed Transformation of Rice," The Plant Journal, 2006, pp. 969-976, vol. 47.

Dubouzet, J.G. et al, "Ine-Nazuna FOX Keito 2 Man Keito yori Senbatsu sareta Byogen Saikin Pst3000 Kansen Teikosei Idenshi no Kaiseki," Dai 49 Kai Proceedings of the Annual Meeting of the Japanese Society of Plant Physiologists, Mar. 15, 2008, p. 336, Abstract P397(932). ). (Please see International Search Report as a concise Explanation of the Relevance).

Ichikawa, T. et al., "The FOX Hunting System: An Alternative Gain-of-Function Gene Hunting Technique," The Plant Journal, 2006, pp. 974-985, vol. 48, No. 6.

Kanno, M. et al., "Ine-Shiroinunazuna FOX Keito o Mochiita Ine no Yudo Teikosei ni Kan'yo suru Shinki Inshi no Tansaku," Dai 49 Kai Proceedings of the Annual Meeting of the Japanese Society of Plant Physiologists, Mar. 15, 2008, p. 335, Abstract P396(931).(Please see International Search Report as a concise Explanation of the Relevance).

Chern, M-S. et al., "Evidence for a Disease-Resistance Pathway in Rice Similar to the NPR-1-Mediated Signaling Pathway in *Arabidopsis*," The Plant Journal, Jul. 2001, pp. 101-113, vol. 27, No. 2.

Datta, K. et al., "Pyramiding Transgenes for Multiple Resistance in Rice Against Bacterial Blight, Yellow Stem Borer and Sheath Blight," Theor. Appl. Genet., 2002, pp. 1-8, vol. 106, No. 1.

Delteil, A. et al., "Potential Candidate Genes for Improving Rice Disease Resistance," Rice, 2010, pp. 56-71, vol. 3.

Narayanan, N.N. et al., "Cell Biology & Molecular Genetics: Molecular Breeding for the Development of Blast and Bacterial Blight Resistance in Rice cv. IR50," Crop Science, Nov. 2002, pp. 2072-2079, vol. 42.

Nishizawa, Y. et al., "Enhanced Resistance to Blast (*Magnaporthe grisea*) in Transgenic Japonica Rice by Constitutive Expression of Rice Chitinase," Theor. Appl. Genet., Aug. 1999, pp. 383-390, vol. 99, No. 3-4.

Qiu, D. et al., "OsWRKY13 Mediates Rice Disease Resistance by Regulating Defense-Related Genes in Salicylate- and Jasmonate-Dependent Signaling," Molecular Plant-Microbe Interactions, May 2007, pp. 492-499, vol. 20, No. 5.

Sawada, K. et al., "Enhanced Resistance to Blast Fungus and Bacterial Blight in Transgenic Rice Constitutively Expressing OsSBP, a Rice Homologue of Mammalian Selenium-Binding Proteins," Biosci. Biotechnol. Biochem., Apr. 2004, pp. 873-880, vol. 68, No. 4.

Tabei, Y. et al., "Transgenic Cucumber Plants Harboring a Rice Chitinase Gene Exhibit Enhanced Resistance to Gray Mold (*Botrytis cinerea*)," Plant Cell Reports, 1998, pp. 159-164, vol. 17, No. 3.

Wally, O. et al., "Genetic Engineering for Increasing Fungal and Bacterial Disease Resistance in Crop Plants," GM Crops, Jul./Aug./Sep./Oct. 2010, pp. 199-206, vol. 1, No. 4.

Wang, G-L. et al., "The Cloned Gene, Xa21, Confers Resistance to Multiple *Xanthomonas oryzae* pv. Oryzae Isolates in Transgenic Plants," Molecular Plant-Microbe Interactions, 1996, pp. 850-855, vol. 9, No. 9.

\* cited by examiner

RICE GENE CAPABLE OF IMPARTING WIDE-SPECTRUM DISEASE RESISTANCE

TECHNICAL FIELD

The present invention relates to methods for producing plants which provide resistance against either a pathogenic bacterium or a pathogenic fungus, or both, plants that are obtained using these methods, and uses thereof.

BACKGROUND ART

Disease-inflicted damages on rice production are significant. In the field of agriculture, while agrochemicals are used for disease control, due to concerns regarding the cost of agrochemicals and their effects on the human body and the environment, rice cultivation with no or little use of agrochemicals is desirable. In particular, methods utilizing genes are thought to be effective, and in recent years, disease-resistance genes have been isolated from Arabidopsis thaliana—a model plant. However, since screening for disease-resistance genes has been carried out mainly using loss-of-function as the indicator, many important genes may have been overlooked.

Meanwhile, in the disease response of Arabidopsis thaliana, there is a signal transduction pathway in which salicylic acid (SA) functions as a signal molecule, and this molecular mechanism is being studied in detail. When a pathogen infects Arabidopsis thaliana, the intracellular SA concentration increases, causing induction of disease response reactions, which include changes in expression of a large number of genes including the PR genes, which are regulated downstream of SA in the signal transduction pathway. Furthermore, external treatment of SA or its derivative INA (2,6-dichloroisonicotinic acid) causes activation of the SA signal transduction system and induction of expression of the downstream-regulated disease-resistance genes and the PR genes.

In the SA signal transduction system, the NPR1 protein plays an important role (Non-Patent Document 2). It is known that in the npr1 mutant of Arabidopsis thaliana, induction of expression of the disease-resistance genes and the PR genes by SA or INA is not observed, and the mutant cannot also be grown on a medium containing SA. However, when it comes to rice, findings relating to the SA signal transduction pathway and signal transduction factors involved in this pathway are extremely limited.

Prior art documents of the present invention are shown below.

[Non-Patent Document 1] Becker, D et al., (1990) Nucleic Acid Res., 18(1): 203.
[Non-Patent Document 2] Cao, H et al (1997) Cell 88:57-63.
[Non-Patent Document 3] Ichikawa, T et al., (2006) Plant J. 48: 974-985.
[Non-Patent Document 4] Kikuchi, S et al., (2003) Science 301: 376-379.
[Non-Patent Document 5] Mori, M et al., (2007) Plant Mol. Biol., 63:847-860.
[Non-Patent Document 6] Nakamura, H et al., (2007) Plant Mol Biol. 65:357-371.
[Non-Patent Document 7] Taji, T et al., (2002) Plant J., 29(4): 417-426.
[Non-Patent Document 8] Toki, S et al., (2006) Plant J. 47:969-76.

DISCLOSURE OF THE INVENTION

Problems to be Solved by the Invention

The present invention was achieved in view of the above circumstances. An objective of the present invention is to isolate a novel gene capable of imparting wide-spectrum disease resistance.

Means for Solving the Problems

To solve the above-mentioned problems, identification of genes that confer resistance against pathogenic bacteria and pathogenic fungi was attempted by screening based on gain-of-function instead of using loss-of-function as the indicator. Specifically, the present inventors attempted screening with the three steps of selection for resistance to pathogenic bacteria infection, selection for resistance to pathogenic fungi infection, and selection for salicylic acid sensitivity on Arabidopsis thaliana lines that highly express rice full-length cDNA (rice-FOX Arabidopsis lines), which were prepared by using the FOX hunting system. As a result, the present inventors successfully discovered one Arabidopsis thaliana line (line K15424) which was selected in all of the three types of screening. Line K15424 carries a rice full-length cDNA (AK070024, a novel protein kinase gene). The present inventors generated rice overexpressing AK070024, and examined the resistance against rice bacterial leaf blight in the T1 generation. As a result, it was confirmed that AK070024-overexpressing rice is resistant against bacterial leaf blight and blast.

The present invention relates to an unprecedented gene which imparts resistance against pathogenic bacteria and pathogenic fungi, and plants into which this gene was introduced. More specifically, the present invention provides [1] to [7] below.

[1] a method for imparting to a plant resistance against either a pathogenic bacterium or a pathogenic fungus, or both; wherein the method comprises the steps of:
  (a) introducing into a plant cell a DNA selected from the group consisting of (i) to (iv) below or a vector comprising the DNA; and
  (b) regenerating a plant from the plant cell into which a DNA or a vector was introduced in step (a);
    (i) a DNA encoding a protein comprising the amino acid sequence of SEQ ID NO: 2;
    (ii) a DNA comprising a coding region of the nucleotide sequence of SEQ ID NO: 1;
    (iii) a DNA encoding a protein comprising an amino acid sequence with one or more amino acid substitutions, deletions, additions, and/or insertions in the amino acid sequence of SEQ ID NO: 2; and
    (iv) a DNA that hybridizes under stringent conditions with a DNA comprising the nucleotide sequence of SEQ ID NO: 1;

[2] a plant cell into which a DNA of any one of (a) to (d) below or a vector comprising the DNA has been introduced, wherein the plant cell can regenerate a plant which is resistant against either a pathogenic bacterium or a pathogenic fungus, or both:
  (a) a DNA encoding a protein comprising the amino acid sequence of SEQ ID NO: 2;
  (b) a DNA comprising the coding region of the nucleotide sequence of SEQ ID NO: 1;
  (c) a DNA encoding a protein comprising an amino acid sequence with one or more amino acid substitutions, deletions, additions, and/or insertions in the amino acid sequence of SEQ ID NO: 2; and (d) a DNA that hybridizes under stringent conditions with a DNA comprising the nucleotide sequence of SEQ ID NO: 1;

[3] a plant resistant to either a pathogenic bacterium or a pathogenic fungus, or both, which plant has been regenerated from the plant cell of [2];

[4] a plant resistant to either a pathogenic bacterium or a pathogenic fungus, or both, which plant is a progeny or a clone of the plant of [3];

[5] a propagation material of the plant [3] or [4] which is resistant to either a pathogenic bacterium or a pathogenic fungus, or both;

[6] a method for producing a plant which is resistant to either a pathogenic bacterium or a pathogenic fungus, or both, wherein the method comprises the steps of:
  (a) introducing into a plant cell a DNA selected from the group consisting of (i) to (iv) below or a vector comprising the DNA; and
  (b) regenerating a plant from the plant cell into which a DNA or a vector was introduced in step (a);
    (i) a DNA encoding a protein comprising the amino acid sequence of SEQ ID NO: 2;
    (ii) a DNA comprising the coding region of the nucleotide sequence of SEQ ID NO: 1;
    (iii) a DNA encoding a protein comprising an amino acid sequence with one or more amino acid substitutions, deletions, additions, and/or insertions in the amino acid sequence of SEQ ID NO: 2; and
    (iv) a DNA that hybridizes under stringent conditions with a DNA comprising the nucleotide sequence of SEQ ID NO: 1; and

[7] a method of screening for a candidate compound for a pharmaceutical agent which imparts to a plant resistance against either a pathogenic bacterium or a pathogenic fungus, or both, wherein the method comprises the steps of:
  (a) contacting a test compound with a cell or a cell extract comprising a DNA having a structure in which all or a part of the nucleotide sequence of SEQ ID NO: 3 is operably linked with a reporter gene;
  (b) measuring the expression level of the reporter gene; and
  (c) selecting a compound that increases the expression level compared to the expression level measured in the absence of the test compound.

MODE FOR CARRYING OUT THE INVENTION

Figure 1:
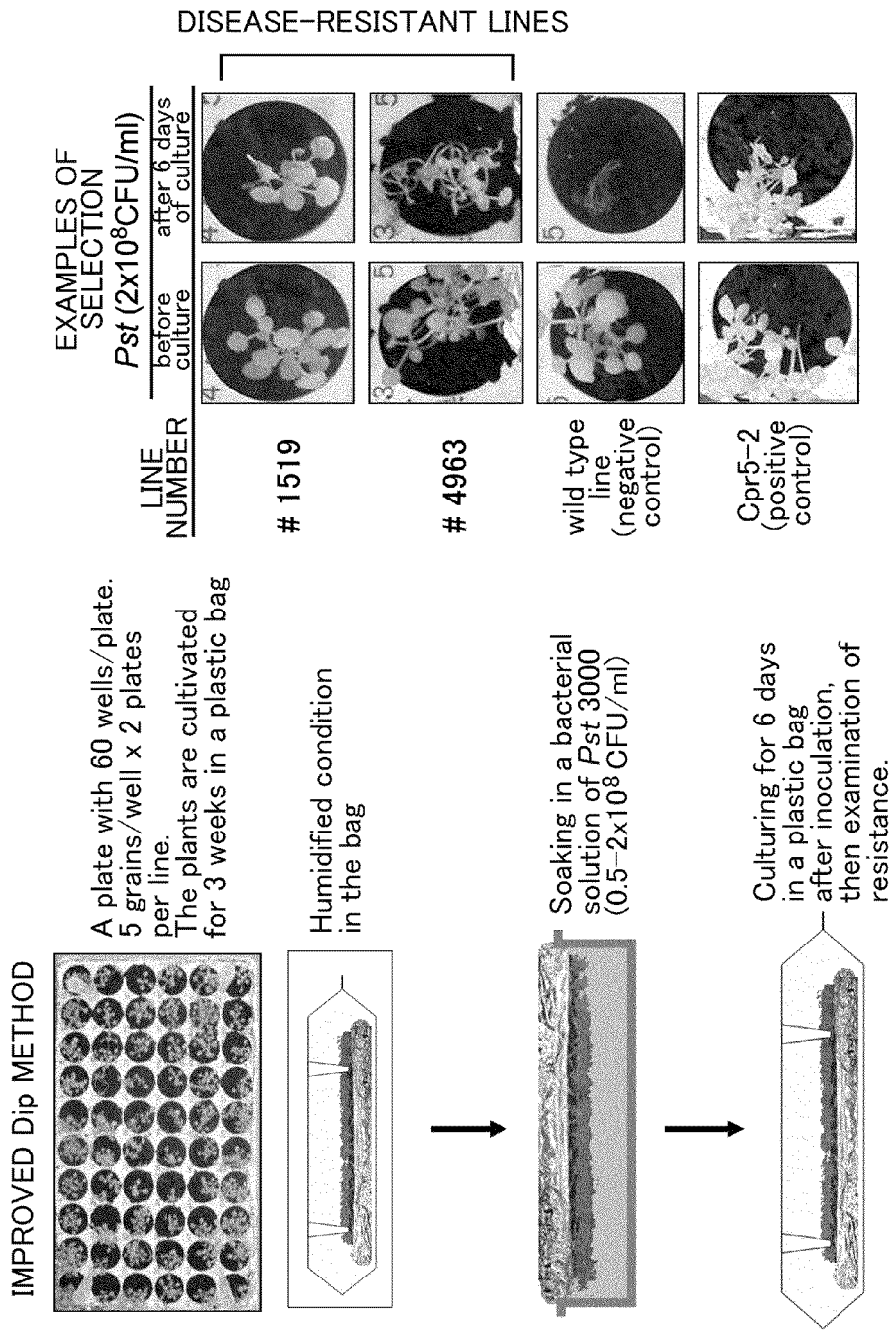
FIG. 1 shows the method for selecting rice-FOX *Arabidopsis* lines using Pst3000 (improved Dip method) and examples of the selection. Columbia (Col-0) was used for the wild type in the examples of the selection. Cpr5-2 was used as a known disease-resistant mutant control.

The present invention provides methods of imparting to a plant resistance against a pathogenic bacterium or a pathogenic fungus, or both, by using a protein kinase gene (DDBJ Accession No: AK070024).

Examples of the pathogenic bacteria in the present invention include bacteria causing leaf spots of tomato, leaf blight of rice, damping-off of rice seedling, and grain rot of rice, but are not limited thereto. Furthermore, examples of the pathogenic fungi of the present invention include anthracnose fungi of cruciferous vegetables, blast fungi, and powdery mildew fungi, but are not limited thereto.

Whether or not a plant has resistance to a pathogenic bacterium or a pathogenic fungus can be evaluated by culturing the pathogenic bacterium or the pathogenic fungus, and then soaking the plant in a bacterial/fungal solution or by spraying the bacterial/fungal solution on a plant.

The form of the DNAs used in the present invention is not particularly limited, and it may be a cDNA or genomic DNA. Genomic DNAs and cDNAs can be prepared by using conventional means known to one skilled in the art. For example, genomic DNA can be prepared by designing an appropriate primer pair from the known nucleotide sequence of the protein kinase gene (DDBJ Accession No: AK070024) (SEQ ID NO: 1), performing PCR using genomic DNA prepared from a plant of interest as template, and screening genomic libraries using the resulting amplified DNA fragment as probe. Further, a cDNA encoding the protein kinase of the present invention can be prepared by similarly designing a primer pair, performing PCR using cDNAs or mRNAs prepared from a plant of interest as template, and screening cDNA libraries using the resulting amplified DNA fragment as probe. The DNAs of interest may also be synthesized using a commercially available DNA synthesizer.

Not only DNAs encoding the rice-derived protein kinase (SEQ ID NO: 2), but also DNAs encoding proteins that are structurally similar to the protein (e.g., mutants, derivatives, alleles, variants, and homologs) can be used as DNA of the present invention, as long as they have the function of imparting to plants resistance against either a pathogenic bacterium or a pathogenic fungus, or both. Such DNAs include, for example, DNAs encoding a protein containing an amino acid sequence with one or more amino acid substitutions, deletions, additions, and/or insertions in the amino acid sequence of SEQ ID NO: 2.

Examples of methods well-known in the art for preparing DNAs encoding a protein with altered amino acid sequence include site-directed mutagenesis methods (Kramer, W. and Fritz. H. J., Oligonucleotide-directed construction of mutagenesis via gapped duplex DNA, Methods Enzymol. 154, 1987, 350-367). In nature, mutations in nucleotide sequences may also lead to mutations in the amino acid sequences of proteins encoded thereby. As described above, DNAs encoding a protein having an amino acid sequence with one or more amino acid substitutions, deletions, or additions in the amino acid sequence of the naturally-occurring protein kinase (SEQ ID NO: 2) are included in the DNAs of the present invention, as long as they have the function of imparting to plants resistance against either or both of a pathogenic bacterium and a pathogenic fungus.

The number of amino acids to be altered is not particularly limited, but is generally 50 or less, preferably 30 or less, more preferably 10 or less (e.g., 5 or less, or 3 or less). Alterations of amino acids are preferably conservative substitutions. The hydropathic indices (Kyte, J. and Doolittle, R. F., J. Mol. Biol. 157(1), 1982, 105-132) and hydrophilicity values (U.S. Pat. No. 4,554,101) for each amino acid before and after an alteration are preferably within ±2, more preferably within ±1, and most preferably within ±0.5.

In addition, mutations in a nucleotide sequence are not always accompanied by mutations in the amino acids of the protein (i.e., degenerate mutations). Such degenerate mutants are also included in DNAs of the present invention.

DNAs encoding proteins that are structurally similar to the rice-derived protein kinase (SEQ ID NO: 2) can be prepared by using hybridization techniques (Southern, E. M., J. Mol. Biol. 98, 1975, 503) and polymerase chain reaction (PCR) (Saiki, R. K. et al., Science 230, 1985, 1350-1354; and Saiki, R. K. et al., Science 239, 1988, 487-491). That is, the DNAs of the present invention include DNAs that hybridize under stringent conditions to the DNA consisting of the nucleotide sequence of SEQ ID NO: 1. For isolating such DNAs, hybridization reactions are preferably performed under stringent conditions. In the present invention, the term "stringent conditions" refers to the conditions of 6 M urea, 0.4% SDS, and 0.5×SSC, and hybridization conditions of equivalent stringency, without being limited thereto. Conditions of higher stringency such as 6 M urea, 0.4% SDS, and 0.1×SSC can be expected to lead to isolation of DNAs of higher homologies.

A variety of factors such as temperature and salt concentration are considered as factors that affect hybridization stringency. However, one skilled in the art can establish optimal stringencies by appropriately selecting these factors. The DNAs isolated by the above-described hybridizations at the amino acid level are considered to have a high homology with the amino acid sequence of the rice-derived protein kinase (SEQ ID NO: 2). The term "high homology" refers to identities of at least 50% or more, more preferably 70% or more, most preferably 90% or more (e.g., 95%, 96%, 97%, 98%, 99%, or more) over the entire amino acid sequence. Amino acid sequence identities and nucleotide sequences identities can be determined by using BLAST algorithm by Karlin and Altschul (Karlin, S. and Altschul, S. F., Proc. Natl. Acad. Sci. USA 87(6), 1990, 2264-2268; and Karlin, S. and Altschul, S. F., Proc. Natl. Acad. Sci. USA 90(12), 1993, 5873-5877). BLASTN and BLASTX programs have been developed based on the BLAST algorithm (Altschul, S. F. et al., J. Mol. Biol. 215(3), 1990, 403-410). When nucleotide sequences are analyzed using BLASTN, parameters are set to be, for example, score=100 and wordlength=12. When amino acid sequences are analyzed using BLASTX, parameters are set to be, for example, score=50 and wordlength=3. When BLAST and Gapped BLAST programs are used, default parameters for the respective program are used. Specific procedures of these analysis methods are publicly known.

The DNAs of the present invention may be inserted into vectors. Vectors are not particularly limited, as long as they can allow introduced genes to be expressed in plant cells. For example, it is possible to use vectors containing promoters for homeostatic gene expressions in plant cells (e.g., the promoter of the potato SK2 chitinase gene, the cauliflower mosaic virus 35S promoter, etc.), or vectors containing promoters that are inducibly activated by external stimulation.

The protein coding region in the nucleotide sequence of SEQ ID NO: 1 is the nucleotides from position 34 to position 1251. The amino acid sequence produced from the nucleotides from position 34 to position 1251 in the nucleotide sequence of SEQ ID NO: 1 is shown in SEQ ID NO: 2.

A plant which is resistant against either a pathogenic bacterium or a pathogenic fungus, or both, can be produced by introducing into a plant cell the above-mentioned DNA having the function of imparting to a plant resistance against either a pathogenic bacterium or a pathogenic fungus, or both, or introducing a vector comprising such a DNA, and regenerating a plant from the plant cell. Therefore, the present invention provides methods for producing a plant which is resistant to pathogenic bacteria and/or pathogenic fungi.

The types of plant cells into which the above-mentioned DNA or vector is introduced include monocots such as rice, wheat, barley, corn, and sorghum, and dicots such as *Arabidopsis thaliana*, rapeseed, tomato, soybean, and potato, but are not limited thereto.

Plant cells into which the aforementioned DNAs or vectors are introduced are not particularly limited and may be in any form as long as they can be used to regenerate plants. For example, suspension-cultured cells, protoplasts, leaf sections and calli can be used.

Introduction of the aforementioned DNAs or vectors into plant cells can be performed using methods known to one skilled in the art, such as polyethylene glycol methods, electroporation, Agrobacterium-mediated methods, and particle gun methods. In the Agrobacterium-mediated methods, for example, according to the method by Nagel et al. (Nagel, R. et al. FEMS Microbiol. Lett. 67, 1990, 325-328), a DNA can be introduced into plant cells by introducing into Agrobacteria an expression vector to which the DNA is inserted, and infecting plant cells with the Agrobacteria via direct infection or by the leaf disc method.

Regeneration of a plant from a plant cell can be carried out according to the type of plant by methods known to those skilled in the art. For instance, an example for rice is the method of Fujimura et al. (Fujimura. et al. Tissue Culture Lett. 2, 1995, 74), examples for wheat include the method of Harris et al. (Harris, R. et al. Plant Cell Reports. 7, 1988, 337-340) and the method of Ozgen et al. (Ozgen, M. et al. Plant Cell Reports. 18, 1998, 331-335), examples for barley include the method of Kihara and Funatsuki (Kihara, M. and Funatsuki, H. Breeding Sci. 44, 1994, 157-160) and the method of Lurs and Lorz (Lurs, R. and Lorz, H. Theor. Appl. Genet. 75, 1987, 16-25), examples for corn include the method of Shillito et al. (Shillito, R. D., et al. Bio/Technology, 7, 1989, 581-587) and the method of Gordon-Kamm et al. (Gordon-Kamm, W. J. et al. Plant Cell. 2(7), 1990, 603-618), and examples for sorghum include the method of Wen et al. (Wen, F. S., et al. Euphytica. 52, 1991, 177-181) and the method of Hagio (Hagio, T. Breeding Sci. 44, 1994, 121-126), but are not limited thereto.

Furthermore, an example for *Arabidopsis thaliana* is the method of Akama et al. (Akama et al. Plant Cell Reports. 12, 1992, 7-11), an example for rapeseed is the method of Wang et al. (Wang, Y. P. et al. Plant Breeding. 124, 2005, 1-4), examples for tomato include the method of Koblitz and Koblitz (Koblitz, H and Koblitz, D. Plant Cell Reports. 1, 1982, 143-146) and the method of Morgan and Cocking (Morgan, A. and Cocking, E. C. Z. Pflanzenpysiol. 106, 1982, 97-104), examples for soybean include the method of Lazzeri et al. (Lazzeri, P. A. et al., Plant Mol. Biol. Rep. 3, 1985, 160-167) and the method of Ranch et al. (Ranch, J. P. et al., In Vitro Cell Dev. Biol. 21, 1985, 653-658), and an example for potato is the method of Visser et al. (Visser, R. G. F. et al. Theor. Appl. Genet. 78, 1989, 594-600), but are not limited thereto.

Once a plant transformed through the insertion of an aforementioned DNA or vector into its genome is obtained, it is possible to obtain progenies or clones from that plant by sexual or asexual reproduction. In addition, propagating materials (such as seeds, fruits, panicles, tubers, root tubers, lines, calli, protoplasts, etc.) can be obtained from the plant, or progenies or clones thereof, and used for large-scale production of the plant.

Whether or not a plant has resistance against either a pathogenic bacterium or a pathogenic fungus, or both, can be determined by comparing to a control. In the present invention, a control refers to a plant of the same species as the plant of the present invention, in which a DNA of the present invention is not overexpressed. A control in the present invention is not particularly limited as long as it is a plant of the same species as the plant of the present invention, in which a DNA of the present invention is not overexpressed. Therefore, a control in the present invention includes, for example, a plant into which a DNA other than the DNA encoding the rice-derived protein kinase of the present invention has been introduced. Examples of such a plant include plants of the same species as the transformed plants of the present invention, which are transformed with a DNA other than the DNA of the present invention, plants transformed with a DNA of the present invention into which a functional deletion mutation has been introduced, plants transformed with a DNA produced by converting the DNA of the present into a functionally-suppressed form, and plants transformed with a DNA fragment of a region of the DNA of the present invention which is insufficient for functional expression, but are not limited thereto.

Accordingly, the present invention also provides plants showing resistance against either a pathogenic bacterium or a pathogenic fungus, or both, plant cells which may regenerate the plants, plants which are progenies or clones of the plants, and propagation materials of the above-mentioned plants.

Furthermore, the plants, plant cells, plants which are progenies or clones, and propagation materials of the present invention may also have sensitivity to salicylic acid.

Furthermore, the present invention provides methods of screening for candidate compounds of pharmaceutical agents that impart to plants resistance against either or a pathogenic bacterium or a pathogenic fungus, or both.

In this method, first, a test compound is brought into contact with a cell or a cell extract containing a DNA having a structure in which a DNA containing all or a part of the upstream 2000 bp of the AK070024 gene, including the transcription regulatory region of the AK070024 gene, is operably linked with a reporter gene. Herein, "operably linked" means that a DNA containing all or a part of the upstream 2000 bp of the AK070024 gene, including the transcription regulatory region of the AK070024 gene, is linked with a reporter gene in a manner that expression of the reporter gene is induced by the binding of a transcription factor to the transcription regulatory region of the AK070024 gene. Therefore, even if the reporter gene is bound to a different gene and forms a fusion protein with another gene product, as long as expression of the fusion protein is induced through the binding of a transcription factor to the transcription regulatory region of the AK0700024 gene, such will be included in the meaning of the above-mentioned "operably linked".

The nucleotide sequence of the upstream 2000 bp of the AK070024 gene is shown in SEQ ID NO: 3.

The reporter gene used in the present method is not particularly limited as long as its expression is detectable, and examples include the CAT gene, lacZ gene, luciferase gene, and GFP gene. Examples of a "cell containing a DNA having a structure in which the transcription regulatory region of the AK070024 gene is operably linked with a reporter gene" include cells into which a vector inserted with such a structure has been introduced. Such a vector can be produced by methods well known to those skilled in the art. Vectors can be introduced into cells by common methods, for example, calcium phosphate precipitation method, electroporation, lipofectamine method, and microinjection method. The "cell containing a DNA having a structure in which the gene transcription regulatory region of the AK070024 is operably linked with a reporter gene" also includes a cell in which this structure has been inserted into the chromosome. Insertion of a DNA structure into a chromosome can be carried out using a method commonly used by those skilled in the art, such as a gene transfer method via Agrobacterium.

A "cell extract containing a DNA having a structure in which the transcription regulatory region of the AK070024 gene is operably linked with a reporter gene" is, for example, a cell extract included in a commercially available in vitro transcription/translation kit to which is added a DNA having a structure in which the transcription regulatory region of the AK070024 gene is operably linked with a reporter gene.

Test compounds used in this method are not particularly limited. Examples include, but are not limited to, single compounds such as naturally-occurring compounds, organic compounds, inorganic compounds, proteins, and peptides, as well as compound libraries, expression products of gene libraries, cell extracts, cell culture supernatants, products of fermentative microorganisms, extracts of marine organisms, and plant extracts.

The "contact" in the present method can be carried out by adding a test compound to a culture solution of a "cell containing a DNA having a structure in which the transcription regulatory region of the AK070024 gene is operably linked with a reporter gene", or by adding a test compound to the above-mentioned commercially available cell extract containing the DNA. When the test compound is a protein, the contact can be carried out, for example, by introducing a DNA vector for expressing the protein into the cells.

In the present method, next, the expression level of the reporter gene is measured. The expression level of the reporter gene can be measured by methods known to those skilled in the art according to the type of the reporter gene. For example, when the reporter gene is a CAT gene, the expression level of the reporter gene can be measured by detecting the acetylation of chloramphenicol by the gene product. When the reporter gene is a lacZ gene, luciferase gene, or GFP gene, the expression level of the reporter gene can be measured by detecting the color development of the pigment compound as a result of the catalytic action of the gene expression product; detecting the fluorescence of the fluorescent compound as a result of the catalytic action of the gene expression product; and detecting the fluorescence of the GFP protein, respectively.

Next, in this method, compounds are selected, which increase the measured expression level of the reporter gene compared to when the expression level is measured in the absence of a test compound. Compounds selected in this manner are candidate compounds of pharmaceutical agents that impart to plants resistance against a pathogenic bacterium and/or a pathogenic fungus.

All prior art references cited in this specification are incorporated herein by reference.

EXAMPLES

Next, the present invention is specifically described with reference to Examples; however, the present invention should not be construed as being limited thereto.

1. Materials and Methods 1-1. Rice-FOX *Arabidopsis* Lines

For the screening, approximately 20,000 rice-FOX *Arabidopsis* lines (15,000 lines from RIKEN and 5,000 lines from Okayama) were used. The rice-FOX *Arabidopsis* lines were generated as follows. Approximately 13,000 types of independent rice full length cDNA (Kikuchi et al. 2003) were prepared as a pool of equivalent proportions of cDNAs (this is called standardization), and the cDNAs were incorporated into expression vectors for *Arabidopsis thaliana*. pBIG2113SF produced by introducing an SfiI cloning site into pBIG2113N (Taji et al. 2002, Becker et al. 1990) was used for the expression vector. Using cDNAs standardized as described above, a cDNA library was produced using agrobacteria (Agrobacterium GV3101), and by transforming *Arabidopsis thaliana* Columbia (Col-0) by the floral dip method using these agrobacteria, rice-FOX *Arabidopsis* lines made of independent plants were generated. T2 seeds were used for the screening.

1-2. Selection for Resistance Against Pathogenic Bacteria Infection

Using *Pseudomonas syringae* pv. tomato strain DC3000 (Pst3000) which is the pathogenic bacterium of bacterial leaf speck of tomato, inoculation was carried out at a bacterial cell concentration of $(0.5$ to $2)\times10^8$ CFU/mL by the improved Dip method (FIG. 1). Three weeks after sowing, the FOX lines were soaked in the above-mentioned bacterial solution, and selection was carried out six days later based on their survival.

1-3. Selection for Resistance Against Pathogenic Fungi Infection

Anthracnose fungus of cruciferous vegetables (*Colletotrichum higginsianum*, Ch) is a fungus which infects using an appressorium and penetration hypha in a manner similar to blast fungi. Since it can also infect *Arabidopsis thaliana*, this fungus was used in the selection for resistance against pathogenic fungi infection. Infection was carried out by the improved dip method which was also used for selection using Pst3000. The conidia concentration in the inoculum was $10^5$ to $10^6$ conidia/mL, and selection was carried out six days after infection based on their survival.

1-4. Selection for Sensitivity to Salicylic Acid (SA)

FOX lines were inoculated into an MS medium containing 0.05 mM SA (+SA medium) and an MS medium not containing SA (−SA medium), and lines that grow on the −SA medium but die after germination on the +SA medium were selected.

1-5. Generation of Transformed Rice

Nipponbare was used for the rice cultivar. pRiceFOX (Nakamura et al., 2007) was used as the expression vector in rice. Rice was transformed by a high-speed transformation method (Toki et al., 2006) using Agrobacterium strain EH105.

1-6. Assay for Resistance Against Bacterial Leaf Blight of Rice

Using the rice bacterial leaf blight bacteria race T7174, assays were carried out by modifying the method of Mori et al. (Mori et al., 2007). The main points of modification are that a young rice leaf blade was cut at approximately 5 cm from the tip and that inoculation was carried out by soaking the cut surface in the bacterial solution.

1-7. Assay for Resistance Against Rice Blast

The assay was carried out by the spray inoculation method (Mori et al. 2007) using the rice blast fungus Kyu89-246 (MAFF101506, race 003.0). Fungal concentration of $2\times10^5$ spore/mL was used to carry out the assay.

2. Results 2-1. Selection for Resistance Against Pathogenic Bacteria Infection

Primary, secondary, and tertiary screenings were carried out on approximately 20,000 rice-FOX *Arabidopsis* lines, and 72 lines showing resistance against Pst3000 were ultimately selected. Genomic DNAs were extracted for all of the selected lines, and the genes were identified by amplifying the inserted rice full-length cDNA by PCR and determining the nucleotide sequence of the ends.

2-2. Selection for Resistance Against Pathogenic Fungi Infection

The 72 lines mentioned above were further assayed for resistance to Ch and examined whether there are lines that show combined resistance against both bacteria/fungi. As a result, 21 lines (29%) showed combined resistance.

2-3. Selection for Sensitivity to Salicylic Acid (SA)

Figure 2:
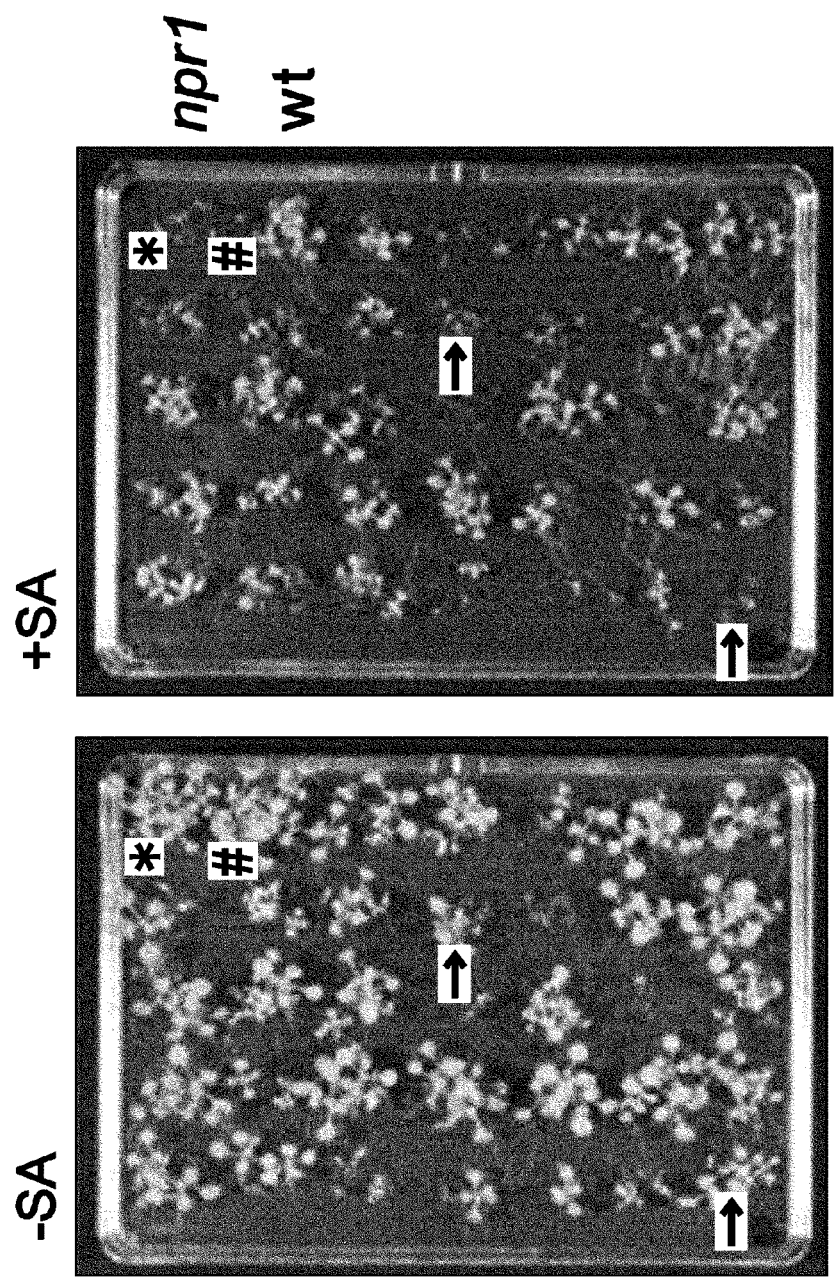
FIG. 2 shows the results of selection for sensitivity to SA (secondary screening) performed on rice-FOX *Arabidopsis* lines. The survival of FOX lines on a medium containing 0.05 mM SA (+SA) and on a medium that does not contain SA (−SA) was investigated. The wild type (Wt) and a highly SA-sensitive mutant (npr1) were used as controls.

First, lines that die on +SA medium were selected from approximately 20,000 rice-FOX *Arabidopsis* lines (primary screening). Secondary screening, which selects lines that die after budding in +SA medium but grow nearly to the same degree as the wild type on −SA medium, was carried out on the selected lines (FIG. 2), and 95 lines were selected. Regarding these lines, the inserted rice full-length cDNAs were amplified by PCR and then the partial nucleotide sequences were determined.

2-4. Line Selected in all Three Types of Screening and its Responsible Gene

There was one line (K15424) which was selected in all of the three types of screening described above. It is very likely that this line has acquired resistance against pathogenic bacteria and pathogenic fungi through an enhanced defense response mechanism in which the SA signal transduction system is involved. A rice full-length cDNA (AK070024) was found to be inserted in the K15424 line. Phylogenic tree analysis of AK070024 revealed that it is closely related to the Novel *Arabidopsis* protein Kinase (NAK) gene, and is a novel protein kinase gene. Furthermore, analyses of other independent FOX lines carrying AK070024 and *Arabidopsis thaliana* with reintroduced cDNA confirmed that overexpression of AK070024 in *Arabidopsis thaliana* imparts Pst3000 resistance, Ch resistance, and SA sensitivity.

2-5. Generation of Overexpressing Rice and Assay on Disease Resistance

Figure 3:
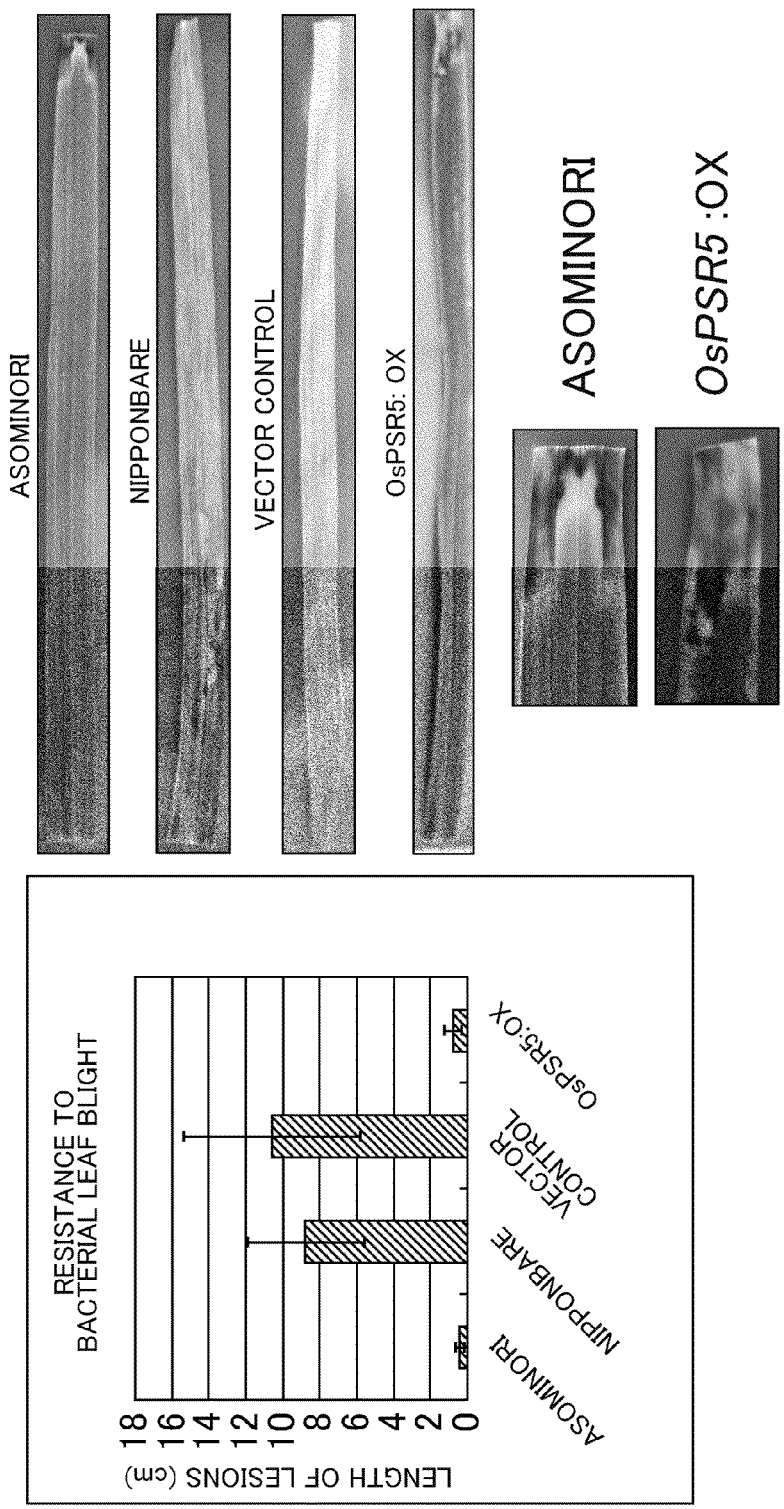
FIG. 3 shows a graph and photographs indicating the resistance against rice bacterial leaf blight in OsPSR5-overexpressing rice. The results obtained two weeks after inoculation of bacterial leaf blight bacteria to the tip of the leaf blade (right end of the photograph) are shown. Asominori is a cultivar having a high level of resistance against bacterial leaf blight. Nipponbare is the Wt. The vector control is a line introduced with pRiceFOX alone. OsPSR5:OX is a rice which overexpresses OsPSR5.
Figure 4:
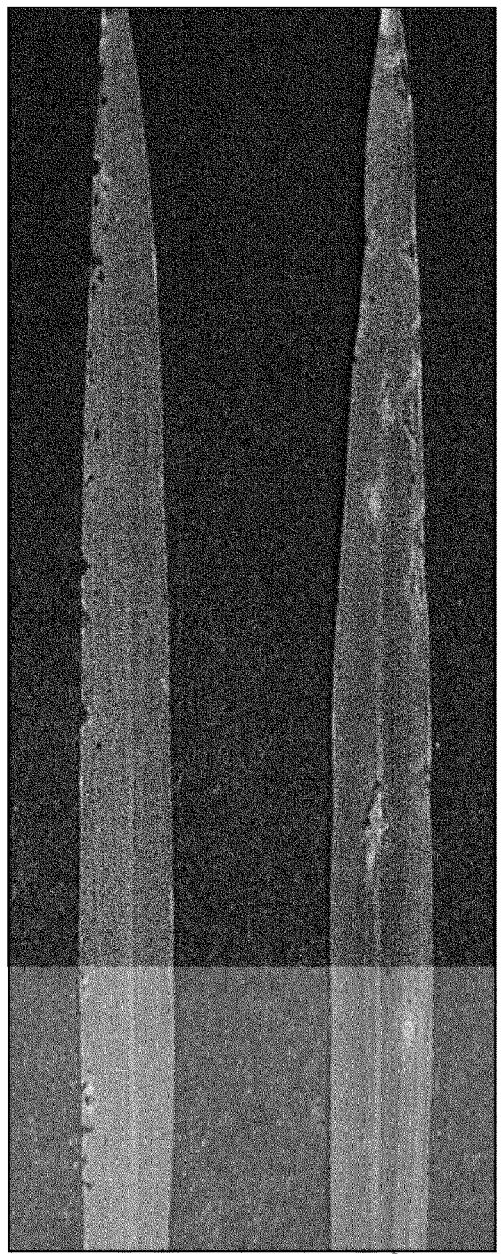
FIG. 4 shows resistance against blast in OsPSR5-overexpressing rice. The photograph was taken on the eighth day after spray inoculation of blast fungus. OsPSR5:OX is a rice which overexpresses OsPSR5. Nipponbare is the Wt.
Figure 5:
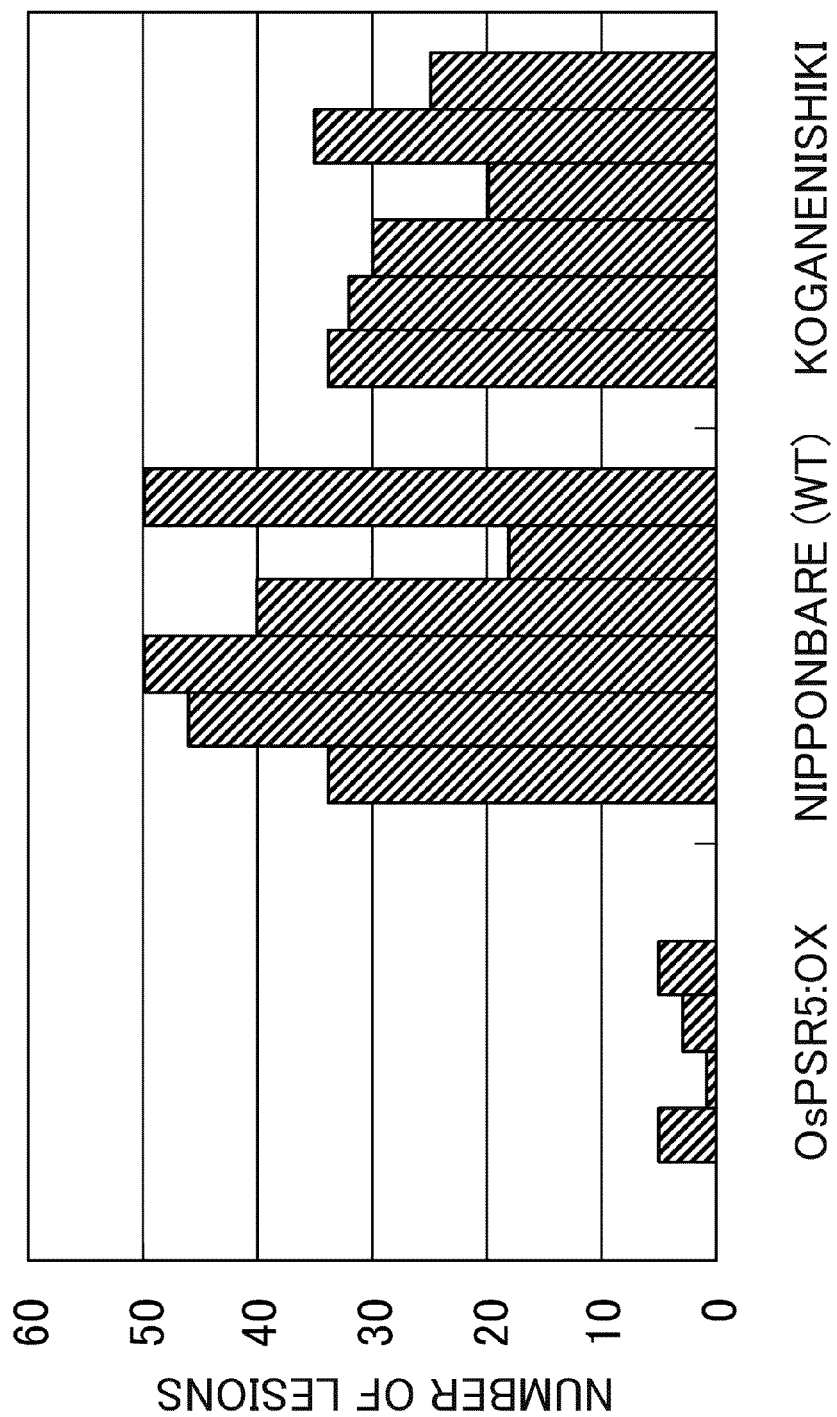
FIG. 5 shows resistance against blast in rice overexpressing OsPSR5. Koganenishiki is a line with slightly stronger resistance compared to Nipponbare (Wt). Fungal inoculation was carried out during the development of the sixth leaf. The number of lesions indicates the total of compatible lesions on the fifth and sixth leaves six days after inoculation.

Rice overexpressing the AK070024 gene (an alternative name is OsPSR5) was produced, and an assay for resistance against bacterial leaf blight of rice was performed on the T1 generation. As a result, the OsPSR5-overexpressing rice showed strong resistance against bacterial leaf blight, which was equivalent to that of the cultivar Asominori which has a strong resistance against bacterial leaf blight (FIG. 3). Similarly, when assay for resistance against blast was performed on OsPSR5-overexpressing rice, after inoculation, the lesion expanded (progressive lesion) in Nipponbare which is the WT, whereas in the overexpressing rice, brown spot-type lesions were found, but the lesions did not expand beyond a certain size. Therefore, it was shown to be resistant against blast as well (FIG. 4). The degree of resistance indicated was stronger than that of Koganenishiki which is more resistant than Nipponbare (FIG. 5).

In the present invention, screening of rice-FOX *Arabidopsis* lines leads to the discovery of a novel gene (AK070024)

which imparts three types of traits: resistance against pathogenic bacteria (Pst3000), resistance against pathogenic fungi (Ch), and a high sensitivity towards salicylic acid. Rice overexpressing this gene showed resistance against bacterial leaf blight and blast. From the above results, plants overexpressing this gene were shown to be resistant against multiple diseases, regardless of whether they are monocots or dicots. This gene may become a material for imparting combined disease resistance to various crops by genetic engineering techniques.

INDUSTRIAL APPLICABILITY

The present invention provides plants that are resistant to pathogenic bacteria and pathogenic fungi. Plants in which the gene identified by the present invention is overexpressed have resistance against multiple diseases, regardless of whether they are monocots or dicots. Therefore, the gene identified in the present invention is useful as a material for imparting combined disease resistance to various crops.

The invention claimed is:

1. A method for imparting to a plant resistance against, or producing a plant which is resistant both a pathogenic bacterium and a pathogenic fungus; wherein the method comprises the steps of:
    (a) introducing into a plant cell a nucleic acid sequence selected from the group consisting of (i) to (iii) below or a vector comprising the nucleic acid sequence, wherein the nucleic acid sequence is operably linked to a heterologous promoter; and
    (b) regenerating a plant from the plant cell into which a nucleic acid sequence or a vector was introduced in step (a);
    (c) obtaining a plant that overexpresses the polynucleotide of (a); and
    (d) verifying resistance to both a pathogenic bacterium and a pathogenic fungus;
        (i) a nucleic acid sequence encoding a protein comprising the amino acid sequence of SEQ ID NO: 2;
        (ii) a nucleic acid sequence comprising the coding region of the nucleotide sequence of SEQ ID NO: 1; and
        (iii) a nucleic acid sequence encoding a protein comprising an amino acid sequence at least 95% identical to the sequence of SEQ ID NO: 2.

2. A plant cell into which a DNA of any one of (a) to (c) below or a vector comprising the DNA has been introduced, wherein said DNA is operably linked to a heterologous promoter, and wherein the plant cell can regenerate a plant which is resistant against both a pathogenic bacterium and a pathogenic fungus:
    (a) a DNA encoding a protein comprising the amino acid sequence of SEQ ID NO: 2;
    (b) a DNA comprising the coding region of the nucleotide sequence of SEQ ID NO: 1; and
    (c) a DNA encoding a protein comprising an amino acid sequence at least 95% identical to the amino acid sequence of SEQ ID NO: 2.

3. A plant resistant to both a pathogenic bacterium and a pathogenic fungus, wherein said plant has been regenerated from the plant cell of claim 2, and wherein said plant comprises said plant cell.

4. A plant resistant to both a pathogenic bacterium and a pathogenic fungus, wherein said plant is a progeny or a clone of the plant of claim 3, and wherein said plant comprises said plant cell.

5. A propagation material of the plant of claim 3 which is resistant to both a pathogenic bacterium and a pathogenic fungus, wherein said propagation material comprises said plant cell.

6. A propagation material of the plant of claim 4 which is resistant to both a pathogenic bacterium and a pathogenic fungus, wherein said propagation material comprises said plant cell.

7. The method of claim 1, wherein the plant cell is rice, wheat, barley, corn, sorghum, *Arabidopsis thaliana*, rapeseed, tomato, soybean, or potato cell.

8. The plant cell of claim 2 which is rice, wheat, barley, corn, sorghum, *Arabidopsis thaliana*, rapeseed, tomato, soybean, or potato cell.

* * * * *

UNITED STATES PATENT AND TRADEMARK OFFICE
CERTIFICATE OF CORRECTION

PATENT NO.         : 9,127,290 B2
APPLICATION NO.    : 13/061396
DATED              : September 8, 2015
INVENTOR(S)        : Masaki Mori et al.

Page 1 of 1

It is certified that error appears in the above-identified patent and that said Letters Patent is hereby corrected as shown below:

In the Claims

Column 17, line 3, after "plant which is resistant", insert --to--.

Column 17, line 29, after "wherein the plant cell", delete "can regenerate a plant" and insert --regenerates a plant--.

Signed and Sealed this
First Day of March, 2016

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 1440
<212> TYPE: DNA
<213> ORGANISM: Oryza sativa

<400> SEQUENCE: 1
ggtgcgtgcg tgcgtgcttg cttgctgcaa gaaatgagct gcttgggttg gttcaagaag      60
cggaggtcgt ccaagagcaa ggaatcgtcg gggaggcggg gctcgacgac gacgacggtg     120
tcggcggtga gcacgagcag gtcggacgac tccggggcgg tgaggccggc gagcaagtcg     180
acggggtcga cgtcgtcgca ccggagcatc tcgtcgctgt acgaggagcg cggccacggc     240
cagctccggg acttcgacta cgacgagctc caggccgcca ccaacggctt cagccgcgcc     300
cagaagctcg gcgagggcgg cttcggcagc gtctacaagg gcttcgtccg ctcctccccc     360
gccgacggca aggccgccga tcgcctcgcc gtcgccgtca agtgcctgaa ccagcggggt     420
ctccagggac ataagcagtg gttggcggaa gtacagttcc ttggggttct tgagcaccca     480
aaccttgtaa agcttcttgg atattgtgcc gttgatggtg aaaggggggcc acaaagatta     540 ttggtgtatg agtatatgcc taataagagc ctggaagatc acttattcgt ccgagcttat     600
cctcctctct catggaatag aaggcttcaa ataatcttgg gtgctgcaga aggattagct     660
tacctgcatg aagggcaagt tcaggtaatc taccgggact tcaaagcatc taacattttg     720
ttggacaaag acttcagagc aaagctgtcg gacttcgggc tagcaaggga gggaccaaca     780
ggagcaaaca ctcacgtctc aacagcggtg gttgggacgc acgggtacgc ggcgccggac     840
tacatagaga cggggcacct gacggtgaag agcgacgtgt ggagcttcgg ggtggtgctg     900
tacgagatcc tgacggggcg gcggacgctg gaccgccacc ggccgcaggg ggagcagaag     960
ctgctggagt gggtcgccca gttcgccccc gacagccgca acttccgcat gatcatggat    1020
cccaggctcc gcggcgagta ctccgtcaag gccgcccgcg acatcgccaa gctcgccgag    1080
tcctgcctcc tcaagaacgc caaggagcgc cccaccatgt ccgaggtcgt cgacgtcctc    1140
cgccgcgccg tccagtcgca gcccgacccc cctcctcccc ccgccgccgc cgccgccgcc    1200
tccggcaagg ggaagagggt cgacgtcgcg ccgcagccgg cgaggaggag gtgaggttgc    1260
actctgctgc tatcatcgat cacggcatga atgaagaaag aaaagtacag aaagagagac    1320
acagagacga gttggtggat tcttggcgtt tttgttttt gttttccttt ctatttttta    1380
ggcttattta ggatgaggat agtagtatga gaatacattt gatttgattg gtagataact    1440

<210> SEQ ID NO 2
<211> LENGTH: 406
<212> TYPE: PRT
<213> ORGANISM: Oryza sativa

<400> SEQUENCE: 2
```

```
Met Ser Cys Leu Gly Trp Phe Lys Lys Arg Ser Ser Lys Ser Lys
1               5                   10                  15
Glu Ser Ser Gly Arg Arg Gly Ser Thr Thr Thr Val Ser Ala Val
                20                  25                  30
Ser Thr Ser Arg Ser Asp Asp Ser Gly Ala Val Arg Pro Ala Ser Lys
        35                  40                  45
Ser Thr Gly Ser Thr Ser Ser His Arg Ser Ile Ser Ser Leu Tyr Glu
    50                  55                  60
Glu Arg Gly His Gly Gln Leu Arg Asp Phe Asp Tyr Asp Glu Leu Gln
65                  70                  75                  80
Ala Ala Thr Asn Gly Phe Ser Arg Ala Gln Lys Leu Gly Glu Gly Gly
                85                  90                  95
Phe Gly Ser Val Tyr Lys Gly Phe Val Arg Ser Ser Pro Ala Asp Gly
                100                 105                 110
Lys Ala Ala Asp Arg Leu Ala Val Ala Val Lys Cys Leu Asn Gln Arg
            115                 120                 125
Gly Leu Gln Gly His Lys Gln Trp Leu Ala Glu Val Gln Phe Leu Gly
        130                 135                 140
Val Leu Glu His Pro Asn Leu Val Lys Leu Leu Gly Tyr Cys Ala Val
145                 150                 155                 160
Asp Gly Glu Arg Gly Pro Gln Arg Leu Leu Val Tyr Glu Tyr Met Pro
                165                 170                 175
Asn Lys Ser Leu Glu Asp His Leu Phe Val Arg Ala Tyr Pro Pro Leu
            180                 185                 190
Ser Trp Asn Arg Arg Leu Gln Ile Ile Leu Gly Ala Ala Glu Gly Leu
        195                 200                 205
Ala Tyr Leu His Glu Gly Gln Val Gln Val Ile Tyr Arg Asp Phe Lys
    210                 215                 220
Ala Ser Asn Ile Leu Leu Asp Lys Asp Phe Arg Ala Lys Leu Ser Asp
225                 230                 235                 240
Phe Gly Leu Ala Arg Glu Gly Pro Thr Gly Ala Asn Thr His Val Ser
                245                 250                 255
Thr Ala Val Val Gly Thr His Gly Tyr Ala Ala Pro Asp Tyr Ile Glu
            260                 265                 270
Thr Gly His Leu Thr Val Lys Ser Asp Val Trp Ser Phe Gly Val Val
        275                 280                 285
Leu Tyr Glu Ile Leu Thr Gly Arg Arg Thr Leu Asp Arg His Arg Pro
    290                 295                 300
Gln Gly Glu Gln Lys Leu Leu Glu Trp Val Ala Gln Phe Ala Pro Asp
305                 310                 315                 320
Ser Arg Asn Phe Arg Met Ile Met Asp Pro Arg Leu Arg Gly Glu Tyr
                325                 330                 335
Ser Val Lys Ala Ala Arg Asp Ile Ala Lys Leu Ala Glu Ser Cys Leu
            340                 345                 350
Leu Lys Asn Ala Lys Glu Arg Pro Thr Met Ser Glu Val Val Asp Val
        355                 360                 365
Leu Arg Arg Ala Val Gln Ser Gln Pro Asp Pro Pro Pro Pro Ala
    370                 375                 380
Ala Ala Ala Ala Ser Gly Lys Gly Lys Arg Val Asp Val Ala Pro
385                 390                 395                 400
Gln Pro Ala Arg Arg
                405
```

```
<210> SEQ ID NO 3
<211> LENGTH: 2000
<212> TYPE: DNA
<213> ORGANISM: Oryza sativa

<400> SEQUENCE: 3
aaacacatgg catatatgca agtaaacaat atcaaaaatc gtcgaacaaa acatgaatta        60
agctacgagc ctatgaataa tatatatcac tataatctat gttccctctt gactttcgtc       120
acaattattc tcgcgcttgt ggctattgat catcaaaatt atttgggctg ccgacaact        180 tcgatgtata caaggatgga gctaaataga ttatgaaact ctgtaaaaca tagtgataat       240
aaagtttgtt gtggtccata tcagtatata tctgacgaga agattcaatc cacgcgggtg      300
aagatattag agagaaaaag tgtacaccca aatactataa acacatgcaa aataaacgta       360
gctcaactga ttgaattggt gaagtcaact cactcaagtt caaatcttaa acgtaacacg       420
acgcctttac ggctaattag tctttcagtg gtagttgacg tacttatcta gtgagatgta       480
tgtggtgact tcttgaattt taaaatatgt tgatcctagt cttctgaagg tattcataca       540
aatagatttt acgtgtgcat gttataaaca tctacgttta tcctatgttt tttcataaaa       600
aagtagggcc atgtttagat tctaactttt ttcttcaaac ttcaaacttt tcgtcacatt       660 aaacttttttt atactcacga acttctaatt ttttcgttac atcgttccaa tttctttaaa       720
cttttaattt taacgtggaa ctaaacacag gctagaacaa catattcgtt tccctaaaaa       780
atattctcga ttcacactc gcatcaccat cccacagctg ttgttttcat cacgcacgca       840
actcatgcaa agtaaattta aattccatga ttagaaaagg gggctgcgac tgctatacag       900
tgatgcaacc gaacacggcc acctgcagag ccagagagag acgcgcaggc atgcgaattt       960
ggcgaagccg acgaggcgtt cagattcgta gttgagaccc gtacgacgac gcgggcaatc      1020
cacacaacaa aaacccaaca ccaaacagag ccgtccccat cccgcccgcc gagctcacac      1080
cacaccgcgt ccgcgtgcgc ccggtgcgcc ccagcagcag caaccgatca gctgatcaat      1140
caactaccag tctaccacgc accgcgcgtg caacggccac caccggcagc acttaggcca      1200
gcctcaatgc aataaccaga ataatgtact cctacgaagc attaaataaa ctatcatcta      1260
aaataaaaaa aataatatga caaggaaata gagaggaaaa aagaaatatc caagacatag      1320
ttttttcaca atatccaaga catcatatga ataagtagt acttcattaa attgaagtat       1380
gaaaaagtag tgtctaatac ttactttctt gataacgtgg agtttatgga aactatattt      1440
aatgtattgg gctgggtctg gccttatata aaccgtagtg atttattaac atatagttaa      1500
ttatgtattc agtggtaagt gacgtacccg tcgacagcga ggcgcctgtg gtgacttcat      1560
cagtctcttc cagaatttgc cggcacagtc ttcgaagatg ctcataggggg tagggtttgc      1620 gtgcgtgtgt tcatagggggt gagtgcgcgt gcgttgtgaa tgtctgcgtt gtattgtgta      1680
attctaaaaa aatatatatt tgttatttat ttataaatta atataatctt ttaaaacaat      1740
ttttatataa aactttttta gaaacgagag gggtgagttg gcagagccaa ccgggccgac      1800
gcggccgctt catcaaacgt agtactaccc ccgcacgtac gcgccctctt cccctctcct      1860
ctctctcgcc tgccgaaata aatcttggcg agctttctga ttctcccttt gctattgcta      1920
ccttccgcgg ttcacagttc acactgcctc tgcctcctct tcttcgccta caaaaggatt      1980
ttggaccgca cacggttcgc                                                  2000
```